United States Patent [19]
Slavensky

[11] Patent Number: 5,266,096
[45] Date of Patent: Nov. 30, 1993

[54] MICROBIAL COMPOSITION

[75] Inventor: Frank J. Slavensky, Sacramento, Calif.

[73] Assignee: Jeru Ecology, Inc., Sacramento, Calif.

[21] Appl. No.: 837,896

[22] Filed: Feb. 20, 1992

[51] Int. Cl.⁵ .................... C05F 11/08; C09K 17/00
[52] U.S. Cl. ........................................ 71/6; 71/903; 71/904; 435/252.4; 435/252.9
[58] Field of Search .......... 71/6, 7, 903, 904, DIG. 1; 435/252.4, 252.9

[56] References Cited
U.S. PATENT DOCUMENTS 4,563,426  1/1986  Yamada et al. ...................... 435/119
5,147,441  9/1992  Megeed et al. ........................... 71/7

*Primary Examiner*—Ferris Lander
*Attorney, Agent, or Firm*—Rosenbaum & Schwartz

[57] ABSTRACT

A microbial hydrocarbon degrader, soil amendment and growth-promoting composition comprising a mixture of bacteria, termed mystic microbes, which is capable of decomposing cellulose, fixing nitrogen, fighting plant pests and disease, and liberating phosphorous into the soil upon application and mixture to soil. The heterotrophic microbial composition further is capable of degrading hydrocarbons in contaminant events.

6 Claims, 3 Drawing Sheets

MICROBIAL COMPOSITION

BACKGROUND OF THE INVENTION

The present relates generally to microbial compositions for degrading toxins resident in soil and facilitating plant growth and for degrading hydrocarbon contaminants in water. More particularly, the present invention relates to a novel mixture of micro-organisms which are capable of decomposing hydrocarbon contaminants in soil or water.

Microbial compositions are known in the art as soil amendments. These microbial soil amendments are represented by the following patents.

Japanese Patent No. J6 0027672A issued to Nippon Life in 1985 discloses a fertilizer that has nitrogen fixing bacteria, cellulose decomposing bacteria, and disease resisting qualities. The patent does not, however, discuss phosphorous-liberating qualities. Furthermore, the main disadvantage of utilizing this patent's fertilizer is that several bacteria must be inoculated into a nutrient medium to form Culture A, and several different bacteria must be inoculated into a separate nutrient medium to form Culture B. The two cultures are then combined and ready for use. The present invention provides a ready-made mixture of bacteria.

U.S. Pat. No 4,551,164 issued to Tenzer in 1985 shows a combination of a mixture of a bacteria and algae to promote plant growth.

U.S. Pat. No. 4,119,429 issued to Lovness in 1978 discussing a soil-improving combination of micro-organisms, enzymes, bone marrow, yeast, potassium citrate with sway flower and wheat. The micro-organisms include those that fix nitrogen and liberate phosphorous, potassium and trace elements. This patent does not disclose disease and pest fighting qualities nor phosphorous-releasing qualities as does the present invention. Furthermore, the patent discloses this soil supplement for addition to potted plants only. The Mystic Microbe describes a method not only for potted plants and gardens, but also for agricultural use.

U.S. Pat. No. 3,205,060 issued to Lindert in 1965 discusses encapsulated nitrogen-fixing bacteria wherein the capsule includes bactericide to create a good bacteria growing environment around the capsule. The preferred species of nitrogen-fixing bacteria are discussed.

U.S. Pat. No. 3,186,826 issued to de Rendon in 1965 employs a mixture of sulphate-producing bacteria to acidify salt- and alkali-containing soils.

U.S. Pat. No. 2767072 issued to Coanda in 1956 discloses a process for producing a soil regeneration substance by a utilizing a combination of animal paunches, vegetation, phosphates, potash, starch, manure, trace elements suspended in colloid lungs, nitrogen-fixing and cellulose-digesting organisms. The patent does not discuss disease and pest fighting qualities nor phosphorous-liberating qualities as discussed in the present invention.

Bacteria generally fall into several major classes with hundreds of species in each class. The bacteria contained in the mixture of the present invention, which is identified by the reference name Mystic Microbe, which is a mixatroph or a heterotroph, includes three major bacterial groups including cellulose bacteria, nitrogen-fixing bacteria and scripto bacteria. A representative sample of the heterotrophic micro-organism mixture has been deposited with the American Type Culture Collection, 12301 Parklawn Drive, Rockville, Md., 20852, USA and has received designation No. ATCC 55139. Characterization studies of the heterotrophic mixture indicate that the mixture contains Arthrobacteria, lactobacillus, and is believed to contain micrococcus.

Cellulose bacteria decompose plant matter which remains in the soil upon death of the plant. These bacteria decompose the stems, leaves, roots and virtually all vegetable matter into humus. As the cellulose bacteria decompose the plant matter, nitrogen and minerals are liberated, thereby enriching the soil.

Nitrogen-fixing bacteria live throughout the upper layers of the soil. These bacteria fix nitrogen from the air and from various plant and animal residues in the soil. The bacteria also neutralize chemicals in oils from the soil, but die in the process. Multiple applications of nitrogen-fixing bacteria are usually needed depending upon soil condition.

Scripto bacteria fight diseases and use antibiotics which combat fungal diseases, nematodes, root rot and insect infestation.

The three basic types of bacteria, present in the Mystic Microbe mixture, are very important in liberating minerals and nutrients already in the soil. Application of the Mystic Microbe mixatrophic mixture assists in achieving and maintaining balanced soil conditions to supply plants with nutrients and fend off disease and insects. Additionally, the Mystic Microbe mixatrophic mixture may be employed in a soil remediation mode as a precursor to planting or utilization of the soil for an ecosystem base.

The mixatrophic composition of the present invention is cultured in non-debittered brewer's yeast or blood meal in the presence of a glycogen source, such as sugar or molasses. The composition of the present invention is resistant to different PH ranges, but will not survive under highly acidic conditions.

In use, the mixatrophic composition may be used in fields at a rate of 20 to 30 gallons per acre, or in gardens at the rate of approximately ½ gallon per square yard.

SUMMARY OF THE INVENTION

It is a principle object of the present invention to provide a microbial composition which acts as a multi-functional soil amendment to decompose plant matter into humus, act as a nitrogen fixer and produce biologically active substances which combat diseases or insect infestations.

It is another object of the present invention to provide a microbial composition which is capable of acting both as a soil amendment and as a hydrocarbon degrading composition for use with oil spills, oil contamination, or other hydrocarbon contamination events.

These properties are accomplished by the present invention, in which there is a heterotrophic bacterial composition consisting of arthrobacteria, lactobacillus and possibly micrococcus. A comparison of the fatty acid profile of the lactobacillus component with *L. plantarum* and *L.casei* presents a profile which most closely resembles *L. plantarum*. Bacterial characterization of the Arthrobacter component presented a morphology in which the cells are gram positive, pleomorphic rods. No motility was observed. The colonies were bright, yellow, entire, smooth, glistening and became mucoid with age. Characterization of the lactobacillus component on MRS medium reflected a morphology of entire, smooth, glistening, low-convex, circular, pinpoint 3 mm isolated, off white in color. On sheep blood agar, the colonies were entire, smooth, glistening, low-convex, pinpoint to 1 mm and transparent. On trypticase soy agar colonies were the same but slowly developed opacity. The cells were gram positive rods having dimensions of approximately 0.8×2.3 mm in size. The cells are non-spore forming and facultatively anaerobic, non-motile and catalase negative. Growth was better on MRS medium (ATCC median No. 416) then on blood or Trypticase Soy Agar. These characteristics were consistent with the genus Lactobacillus. Whole cell analysis showed the presence of mesodiaminiopimelic acid. Of the lactobacilli which contained mesodiaminiopimelic acid, phenotypic characteristics were most closely like L. planatrum.

DETAILED DESCRIPTION OF THE PREFERRED EMBODIMENTS

Figure 1:
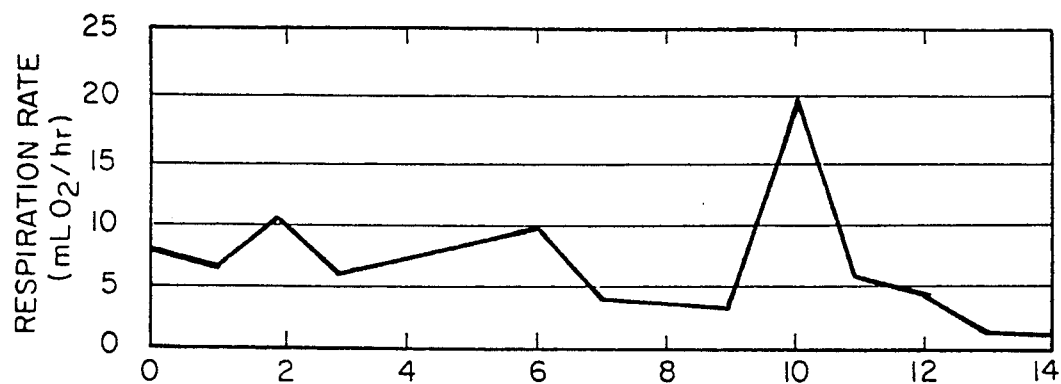
FIG. 1 is a graph of test data reflecting respiration rate of the heterotrophic microbial composition of the present invention over a period of fourteen days.

The novel mixatroph of the subject invention was obtained from a sample of unknown origin growing on waste oil in Sacramento, Calif. The micro-organisms were collected and cultured in 55 gallon plastic drums in water heated to approximately 70 degrees Fahrenheit. The bacterial culture was supplemented with non-debittered brewer's yeast or blood meal and sugar and molasses as a glycogen source. After allowing the mixture to set, the micro-organisms began respiration as evidenced by the release of gas which bubbled through the mixture. The bacterial mixture matured after about 30 hours, or up to 7 days, after mixing, depending upon the temperature. The mixture is viable across a wide range of waters, but is sensitive to highly acidic or highly alkaline water conditions. Diatomaceous earth may be used as a buffer to control the pH.

The heterotrophic micro-organism composition of the present invention was tested for its ability to metabolize perchloroethylene. The micro-organisms of the invention were compared to a commercially available packaged micro-organism sold by Solmar Corporation, under the trademark Solmar CH-118. Solmar CH-118 is supplied as a freeze dried consortium of micro-organisms, which are supposedly acclimated to chlorinated hydrocarbons such as perchloroethylene. The product was presoaked in distilled water at 35 degrees Centigrade for 4 to 6 hours before use and for the test, 25 grams of CH-118 was soaked in 250 ml of water. The heterotrophic micro-organism mixture of the present invention was used in a liquid suspension as previously described.

The two micro-organism solutions were prepared in an equal amount of perchloroethylene added to both. Respirometric activity was monitored for 14 days, with samples taken on days 0, 3, 7, and 14 for analysis by gas chromatography. A third was conducted with no micro-organisms to measure possible volatilization loss of the perchloroethylene from distilled water.

The samples were monitored for respirometric activity in a tech-line respirometer, which measures oxygen consumption as a indicator of metabolism. Output, measured in milliliters of oxygen consumed, is sent to a strip chart recorder. From this chart, respiration in ml of oxygen per hour was calculated.

The Bushnell-Haas medium (ATCC No. 175) was used as a nutrient source because it provides major nutrients and contains no source of food, such as nutrient broth. The Bushnell-Haas medium consist generally of approximately 0.2 grams $MgSO_4.7H_2O$, 0.2 grams $CaCl_2.2H_2O$, 0.1 grams $KH_2PO_4$, 1.0 grams $KH_2PO_4$, 1.0 grams $KH_2PO_4$, 1.0 grams $NH_4NO_3$, and 0.05 grams $FeCl_3.6H_2O$, all measurements taken per liter of distilled water.

A synthetic sewage medium was developed to provide typical waste water organisms with food and nutrients to simulate large respiration rates. The components were mixed and stored dry. The synthetic sewage medium consisted of 40.0 grams of nutrient broth, 4.0 grams urea, 1.4 grams NaCl, 0.4 grams $MgSO_4.7H_2O$, 0.8 grams $CaCl_2.2H_2O$, 3.5 grams $KH_2PO_4$, 3.0 grams $K_2HPO_4$.

Perchloroethylene was provided as Mallinckrodt No. 1933 trichloroethylene.

Sample preparation: Three 2 liter samples were prepared as follows:

A. From a previous trial it was determined that 450 ml of the Mystic Microbe added to 1,550 ml of distilled water would produce an endogenous respiration rate of approximately 20 ml of oxygen per hour. 450 ml of Mystic Microbe, 100 ml of Bushnell-Haas medium and 1,450 ml of distilled water were added to a first sample chamber.

B. Also from a previous trial it was determined that 90 ml of Solmar CH-118 pre-soaked supernatant in 1,910 ml of distilled water would produce an endogenous respiration rate of approximately 20 ml of oxygen per hour. 90 ml of the CH-118 supernatant, 100 ml of the Bushnell-Haas medium, and 1,810 ml of distilled water were added to a second sample chamber.

C. Samples in the Tech-line respirometer were aerated vigorously. Aeration may have caused the PCE to volatilize into the headspace gas causing a decrease in PCE concentration which is not attributable to metabolism. To compensate for this, a third sample chamber was a volatilization control. This third sample chamber was filled with 100 ml of Bushnell-Haas medium and 1,900 ml of distilled water.

D. After all three samples had reached endogenous respiration levels, the samples were moved from the sample chambers and placed in beakers. 4 ml of perchloroethylene were added to each sample. The samples were mixed for 20 minutes after which the excess perchloroethylene was allowed to settle of the bottom of each beaker. Each sample was siphoned from the top and placed back into the respirometers.

E. Three samples were continuously monitored for respirometric activity for 14 days. Respiration rates were determined on days 0, 3, 7, and 14 by withdrawing two, 40 ml aliquots from each sample for gas chromatography analysis in accordance with Environmental Protection Agency Procedure 8021. On day 10, 0.5 grams of synthetic sewage medium was added to each sample as a food source.

Table 1, below, details the test data reflecting respiration rates as milliliters of oxygen generated per hour over the fourteen day test period, data for each of the mystic microbe, SOLMAR CH-118 and distilled water control.

TABLE 1

| Time (Days) | Mystic Microbe (ml $O_2$/hr) | Solmar CH-118 (ml $O_2$/hr) | Distilled Water (ml $O_2$/hr) |
| --- | --- | --- | --- |
| 0 | 7.9 | 7.9 | 0.0 |
| 1 | 6.6 | 3.5 | 0.0 |
| 2 | 10.6 | 2.2 | 0.0 |
| 3 | 6.1 | 1.7 | 0.0 |
| 4 | 7.0 | 0.9 | 0.0 |
| 5 | 8.4 | 1.0 | 0.0 |
| 6 | 9.7 | 1.0 | 0.0 |
| 7 | 4.4 | 1.0 | 1.0 |
| 8 | 6.5 | 1.0 | 1.0 |
| 9 | 3.5 | 1.0 | 1.0 |
| 10 | 20.2 | 3.9 | 5.8 |
| 11 | 6.1 | 2.6 | 1.9 |
| 12 | 4.8 | 1.0 | 1.0 |
| 13 | 1.7 | 1.0 | 1.0 |
| 14 | 1.3 | 1.0 | 1.0 |
| Average Rate | 6.99 | 2.05 | 0.91 |

FIG. 1, which is a graph of respiration rate tests of the mystic microbe, illustrates a fairly constant rate over days one trough six, with decreased respiration days 7-9, and a sharp increase on day 10, reflecting the stimulated respiration due to addition of the synthetic sewage. Days 11 to 14 showed decreased respiration.

Figure 2:
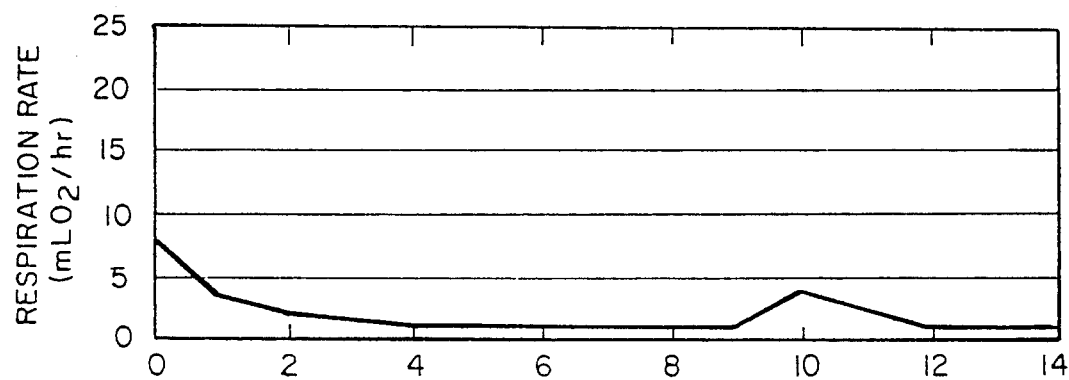
FIG. 2 is a graph of test data reflecting respiration rate of a commercially available heterotrophic microbial composition over a period of fourteen days.

FIG. 2, which is a graph of respiration rate tests of Solmar CH-118, illustrates a rapid decrease of respiration during days 0-3, with a steady rate of during days 4-9. Feeding on day 10 produced an increase in respiration, although the increase failed to reach a level greater than the original respiration rate on day 0. After day 10, the respiration rate fell rapidly back to the level prior to feeding.

Figure 3:
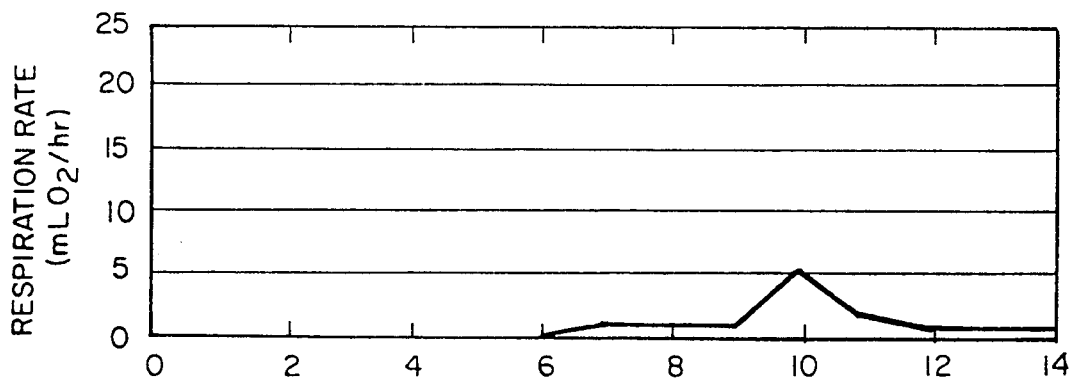
FIG. 3 is a graph of test data reflecting respiration rate of a distilled water control over a period of fourteen days.

FIG. 3 is the control data of the distilled water sample. As expected, the control distilled water sample reflected no respiration during days 0-5. However, on day 6 there was a slight increase in respiration, with a subsequent increase during feeding on day 10. The increased respiration is believed due to contamination.

The data indicate that even though the Mystic Microbe and CH-118 started at the same respiration rate, the Mystic Microbe heterotroph maintained a much higher average respiration rate then the CH-118. To stimulate respiration synthetic sewage was added after day 9 and the respiration of all three samples increased. An increase in respiration was, however, also observed in the distilled water control. The increase in respiration rate in the distilled water is believed due to contamination on day 7 when the sample aliquots were withdrawn.

Table 2 below details the data based on the gas chromatography performed on aliquots of the three samples taken on days 0, 3, 7, and 14. The data is presented for both perchloroethylene and trichloroethylene, the volatilization product of perchloroethylene.

TABLE 2

| Day | Perchloroethylene ppb | Perchloroethylene % | Trichloroethylene ppb | Trichloroethylene % | Total (ppb) |
| --- | --- | --- | --- | --- | --- |
| MYSTIC MICROBE | | | | | |
| 0 | 1328.0 | 100.0 | 0.0 | 0.0 | 1328.0 |
| 3 | 116.3 | 75.7 | 5.4 | 3.5 | 153.6 |
| 7 | 39.0 | 77.8 | 10.1 | 20.2 | 50.1 |
| 14 | 31.6 | 62.8 | 19.8 | 39.4 | 50.3 |
| SOLMAR CH-118 | | | | | |
| 0 | 2550.2 | 92.4 | 0.0 | 0.0 | 2760.0 |
| 3 | 353.0 | 75.1 | 38.5 | 8.2 | 469.8 |
| 7 | 180.7 | 65.0 | 42.3 | 15.2 | 278.1 |
| 14 | 14.0 | 13.7 | 10.4 | 10.2 | 101.9 |
| DISTILLED WATER | | | | | |
| 0 | 3462.5 | 98.36 | 0.0 | 0.0 | 3523.5 |
| 3 | 60.4 | 48.5 | 10.3 | 8.3 | 124.5 |
| 7 | 33.0 | 28.3 | 26.4 | 22.7 | 116.7 |
| 14 | 31.8 | 28.8 | 57.1 | 51.6 | 110.6 |

Figure 4:
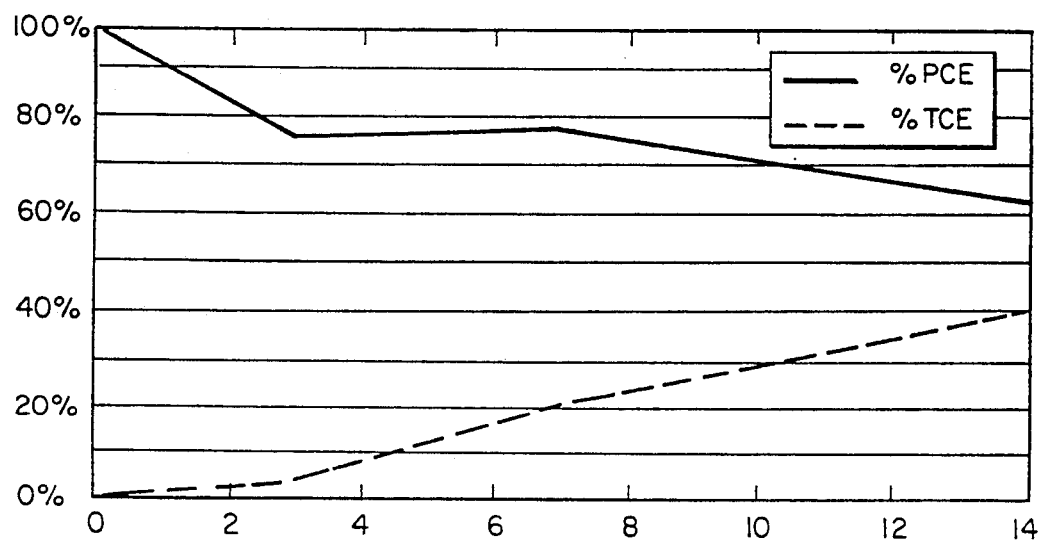
FIG. 4 is a graph of test data of perchloroethylene and trichloroethylene compiled by gas chromatography of the inventive heterotrophic microbial composition over a period of fourteen days.
Figure 5:
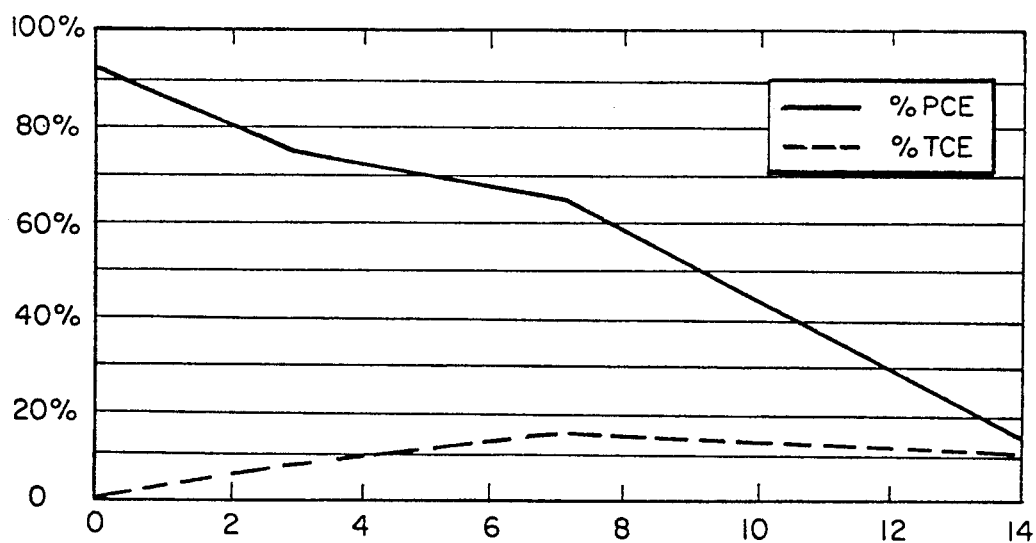
FIG. 5 is a graph of test data of perchloroethylene and trichloroethylene compiled by gas chromatography of the commercially available heterotrophic microbial composition over a period of fourteen days.
Figure 6:
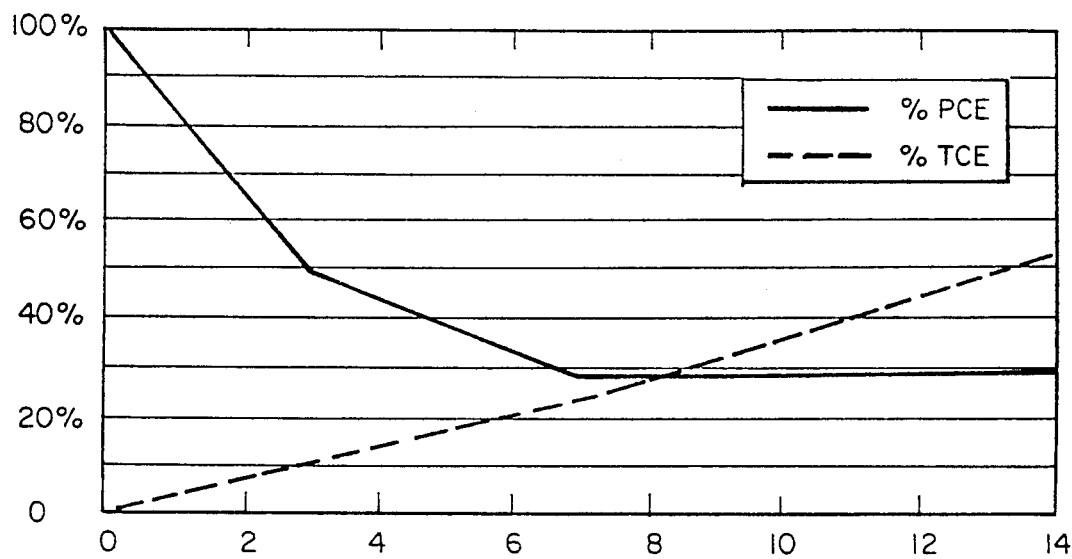
FIG. 6 is a graph of test data of perchloroethylene and trichloroethylene compiled by gas chromatography of the distilled water control over a period of fourteen days.

The data in Table 2 reflects a large volatilization loss of perchloroethylene as trichloroethylene. FIGS. 4-6 graphically present both the perchloroethylene and trichloroethylene concentrations as percent perchloroethylene and percent trichloroethylene of the total concentration for each of the mystic microbe heterotroph (FIG. 4), SOLMAR CH-118 (FIG. 5) and the distilled water control (FIG. 6). In each instance, the perchloroethylene concentration decrease was accompanied by an increase in trichloroethylene.

Perchloroethylene concentration reduction was further calculated by averaging the concentration of perchloroethylene from the PID and Hall detectors. Table 3 lists the data for days 0, 3, 7 and 14.

TABLE 3

| Day | Perchloroethylene (ppb) | Perchloroethylene Reduction (ppb) | Perchloroethylene Reduction (%) |
| --- | --- | --- | --- |
| MYSTIC MICROBE | | | |
| 0 | 1328.0 | 0.0 | 0.0 |
| 3 | 116.3 | 1211.7 | 91.2 |
| 7 | 39.0 | 1289.0 | 97.1 |
| 14 | 31.6 | 1296.4 | 97.6 |
| SOLMAR CH-118 | | | |
| 0 | 2550.2 | 0.0 | 0.0 |
| 3 | 353.0 | 2197.2 | 86.2 |
| 7 | 180.7 | 2369.5 | 92.9 |
| 14 | 14.0 | 2536.2 | 99.5 |
| DISTILLED WATER | | | |
| 0 | 3462.5 | 0.0 | 0.0 |
| 3 | 60.4 | 3402.1 | 98.3 |
| 7 | 33.0 | 3429.5 | 99.0 |
| 14 | 31.8 | 3430.7 | 99.1 |

It will be appreciated from the data in Table 3 that the majority of perchloroethylene reduction occurred in the first three days. The rate constant of perchloroethylene reduction of each sample was determined by a curve fit to the first order non-linear equation:

$$y = C_\phi + C_\infty [1 - e^{-kx}] \quad (1)$$

in which:

x is an independent variable; in this case, time in days;

y is a dependent variable; in this case, percent reduction of perchloroethylene;

$C_{100}$ is the value of y when x equals 0;

$C_\infty$ is the value of y as x equals infinity; and k is the rate constant; this number represents the rate of reaction; in this case metabolism and volatilization.

Using the above equation the rate constant for the mystic microbe heterotroph was 0.918; for SOLMAR CH-118, 0.727; and for the distilled water control 1.602. A linear correlation between the rate constants versus concentration of perchloroethylene for each sample indicates that there is minimal correlation between the rate constants and the initial perchloroethylene concentrations. The lack of statistically significant correlation indicates that variation in rate constants cannot be accounted for by variations in initial perchloroethylene constants.

It is assumed, therefore, that a combination of metabolism and volatilization accounts for the perchloroethylene reduction in the mystic microbe heterotroph and the SOLMAR CH-118 samples, and that volatilization alone accounts for the reduction in the distilled water control.

From the distilled water control, it was noted that the majority of volatilization occurred within the first three days. Accordingly, to enhance observation of perchloroethylene reduction attributable to metabolism, the first three days of data were eliminated. Reduction of perchloroethylene was recalculated from the chromatography data from days 3, 7, and 14, and calculated in parts per billion and as a percent of initial concentration. The results are detailed in Table 4, below.

TABLE 4

| Day | Perchloroethylene (ppb) | Perchloroethylene Reduction (ppb) | Perchloroethylene Reduction (%) |
|---|---|---|---|
| MYSTIC MICROBE | | | |
| 3 | 116.3 | 0.0 | 0.0 |
| 7 | 39.0 | 77.3 | 66.5 |
| 14 | 31.6 | 84.7 | 72.8 |
| SOLMAR CH-118 | | | |
| 3 | 353.0 | 0.0 | 0.0 |
| 7 | 180.7 | 172.3 | 48.8 |
| 14 | 14.0 | 339.0 | 96.0 |
| DISTILLED WATER | | | |
| 3 | 60.4 | 0.0 | 0.0 |
| 7 | 33.0 | 27.4 | 45.4 |
| 14 | 31.8 | 28.6 | 47.4 |

A first order nonlinear curve fit was applied to each reduction figure in accordance with Equation I, above. Rate constants were calculated for the mystic microbe heterotroph as 0.606; for SOLMAR CH-118 as 0.079; and for the distilled water control as 0.551. The rate constants are dramatically different, and percentage reductions observed in the distilled water control were less than the reductions in the two other samples.

Subtracting the distilled water control data from each of the mystic microbe and SOLMAR CH-118 data for perchloroethylene reduction, yielded the data detailed in Table 5.

TABLE 5

| Time (Days) | MYSTIC MICROBE Perchloroethylene Reduction (%) | SOLMAR CH-118 Perchloroethylene Reduction (%) |
|---|---|---|
| 3 | 0.0 | 0.0 |
| 7 | 21.1 | 3.4 |
| 14 | 25.5 | 48.7 |

Figure 7:
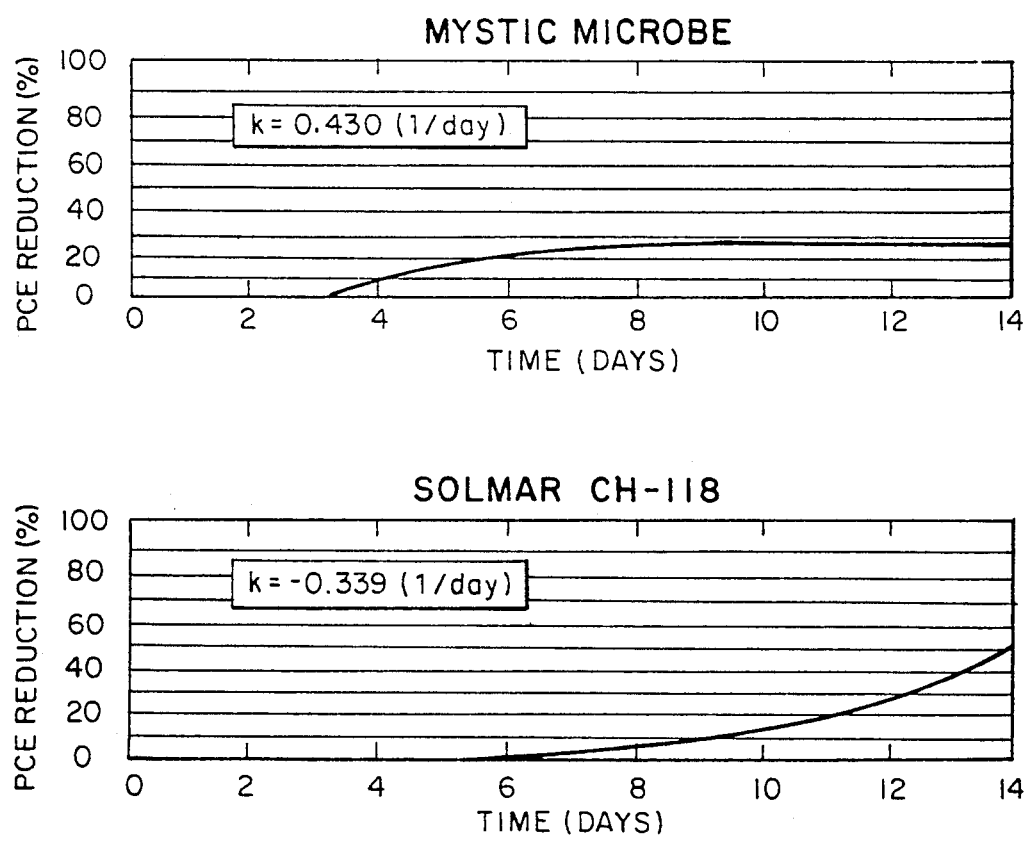
FIG. 7 is a comparative graph of test data of perchloroethylene reduction for the inventive heterotrophic mixture and the commercially available heterotrophic microbial composition, adjusted for the distilled water control.

A first order non-linear curve fit was applied using Equation I, above, and the rate constants calculated for mystic microbe as 0.430 and for SOLMAR CH-118 as −0.339. The curve fits are illustrated in FIG. 7. The negative rate constant for the SOLMAR CH-118 indicates that the curve has a positive concavity, while the mystic microbe curve has a negative concavity, relative to the y-axis. From day 3 to day 12 the inventive heterotroph demonstrated a much larger reduction of perchloroethylene than the commercially available SOLMAR CH-118. In fact, the SOLMAR CH-118 did not begin significant perchloroethylene reduction until day 6. The lag period to day 12 may be indicative of a lack of acclimation of SOLMAR CH-118 to perchloroethylene.

Thus, the inventive heterotrophic mixture, termed mystic microbe, rapidly metabolizes perchloroethylene in the above tests. It is apparent from the test data that the inventive microbial heterotroph more rapidly metabolizes perchloroethylene than a commercially available microbial mixture SOLMAR CH-118, which is sold and used as a soil amendment.

While the tests were run only on perchloroethylene, the test data is believed representative of a general activity of hydrocarbon metabolism. The mystic microbe heterotroph is, therefore, capable of degrading hydrocarbons. To test the capacity of the heterotrophic mixture to metabolize complex hydrocarbons, titers of gasoline in water, diesel fuel in water, waste oil in water and bunker fuel in water were made at serial dilutions of $10^{-1}$ to $10^{-6}$. The inventive heterotroph was diluted with the hydrocarbon titers, plate spread on BiTek Agar and cultured at 25° C. for a period of 480 hours. Background heterotrophic bacteria was $1.4 \times 10^8$ colony forming units per ml of dilute sample. The plates were then examined for the presence of colony growths. The colonies were counted and colony forming units were calculated per milliliter of dilute sample. The results are set forth in Table 6 below, where C.U. indicates colony forming units, n.a. means not applicable, and TNTC means too numerous to count:

TABLE 6

| Contaminant | $10^{-1}$ | $10^{-2}$ | $10^{-3}$ | $10^{-4}$ | $10^{-5}$ | $10^{-6}$ | C.U. |
|---|---|---|---|---|---|---|---|
| Waste Oil | n.a. | 32 | 28 | n.a. | n.a. | n.a. | $4.8 \times 10^3$ |
|  | n.a. | 63 | 19 | n.a. | n.a. | n.a. |  |
| Bunker Fuel | TNTC | 276 | 55 | 9 | 2 | <1 | $5.6 \times 10^4$ |
|  | TNTC | TNTC | 57 | 1 | 1 | <1 |  |
| Gasoline | TNTC | TNTC | TNTC | TNTC | 55 | 12 | $4.7 \times 10^6$ |
|  | TNTC | TNTC | TNTC | TNTC | 38 | 4 |  |
| Diesel Fuel | n.a. | TNTC | TNTC | TNTC | 65 | 5 | $5.3 \times 10^6$ |
|  | n.a. | TNTC | TNTC | TNTC | 41 | 4 |  |

Those skilled in the art will appreciate from the foregoing data, that the inventive heterotrophic bacteria exhibits the ability to metabolize, and hence, degrade hydrocarbons.

In field use, the heterotrophic mixture may be applied from the growth tank to fields at the rate of 20 to 30 gallons per acre with a regular sprayer (garden rates—one half gallon per square yard). It is helpful to then disc or till the bacteria into the soil. On pastoral land, it is best to apply when the soil is wet or apply a more dilute mixture per acre. It may also be applied by allowing the bacteria mixture to drip into irrigation water as it is being applied in the field. The mixture reproduces most rapidly at 70° F., but is resistant to temperature extremes from freezing to hot. Below 70° F. reproduction is slower or, at freezing, it is halted. The bacteria are very hardy and survive in some of the most extreme conditions; when cold it goes into a hibernation effect, and when frozen it remains in stases until thawed, after which its activity returns.

I claim:

1. A heterotrophic bacteria capable of metabolizing hydrocarbon and fixing nitrogen in soil comprising bacteria belonging to the genus Arthrobacteria and bacteria belonging to the genus Lactobacillus, and having all of the identifying characteristics of ATCC No. 55139.

2. The composition according to claim 1, further comprising bacteria belonging to the species L. plantarum.

3. A bacterial heterotroph capable of acting as soil amendment comprising bacteria belonging to the genus Arthrobacteria and bacteria belonging to the genus Lactobacillus, and having all of the identifying characteristics of ATCC No. 55139.

4. The composition according to claim 3, further comprising bacteria belonging to the species L. plantarum.

5. A soil amendment process, comprising the steps of:
   preparing a mixture if water, at least one of yeast or bloodmeal and a glucose source, said mixture comprising about 98-98% by weight water, about 1-2% by weight of said at least one of yeast or bloodmeal, and about 1-2% by weight of said glucose source;
   inoculating said mixture with a heterotrophic bacterial having all of identifying characteristics of ATCC No. 55139;
   allowing said inoculated mixture to set for a period of about 30 hours to about 7 days, until said inoculated mixture begins to release a gas;
   applying said inoculated mixture to soil at a rate of about 20-30 gallons per acre; and
   mixing said applied inoculated mixture with said soil.

6. A method for preparing a microbial plant growth promoting composition, comprising the steps of growing a bacterial culture of a heterotrophic bacteria having all of identifying characteristics of ATCC No. 55139 in a nutrient medium under growth conditions to a cell density of about $4.8 \times 10^3$ to about $1.4 \times 10^8$ cells/ml and diluting said grown heterotrophic bacteria culture with water for application to soil.

* * * * *